United States Patent [19]
Hammer et al.

[11] Patent Number: 6,124,037
[45] Date of Patent: *Sep. 26, 2000

[54] ARTICLES COATED WITH IN VIVO POLYMERIZABLE OPHTHALMIC COMPOSITIONS

[75] Inventors: Mark E. Hammer, Tampa, Fla.; Steven T. Charles, Germantown, Tenn.; John C. Lang, Arlington, Tex.; Robert Y. Lochhead; Lon J. Mathias, both of Hattiesburg, Miss.

[73] Assignees: Alcon Laboratories, Inc., Fort Worth, Tex.; University of Southern Mississippi, Hattiesburg, Miss.

[*] Notice: This patent is subject to a terminal disclaimer.

[21] Appl. No.: 09/012,836

[22] Filed: Jan. 23, 1998

Related U.S. Application Data

[63] Continuation-in-part of application No. 08/833,635, Apr. 8, 1997, Pat. No. 5,858,345, and a continuation-in-part of application No. 08/825,797, Apr. 8, 1997, Pat. No. 5,905,127

[60] Provisional application No. 60/014,925, Apr. 8, 1996, and provisional application No. 60/014,926, Apr. 8, 1996.

[51] Int. Cl.[7] .................. C08F 214/18; C08F 236/16; A61B 17/00; A61F 2/14

[52] U.S. Cl. .................. 428/421; 526/242; 526/245; 526/247; 526/248; 606/1; 623/4; 604/890.1; 514/772.3; 514/772.4; 514/772.6; 514/839; 514/912; 514/915; 424/78.04

[58] Field of Search .................. 424/78.04; 514/772.3, 514/772.4, 772.6, 912, 915, 839; 604/890.1; 526/242, 245, 247, 248, 249; 601/1; 623/4

[56] References Cited

U.S. PATENT DOCUMENTS

| | | | |
|---|---|---|---|
| 5,527,356 | 6/1996 | Peyman et al. | 623/4 |
| 5,858,345 | 1/1999 | Charles et al. | 424/78.04 |
| 5,905,127 | 5/1999 | Lochhead et al. | 526/242 |

FOREIGN PATENT DOCUMENTS

WO 97/00600  1/1997  WIPO.

OTHER PUBLICATIONS

Anderson et al., "Polymerized Lyotropic Liquid Crystals as Contact Lens Materials," *Physica A*, vol. 176, pp. 151–167 (1991).

de Juan, Jr., et al. "Mechanical Retinal Fixation Using Tacks," *Ophthalmology*, vol. 94(4), pp. 337–340 (1987).

de Juan, Jr., et al. "The Use of Retinal Tacks In the Repair of Complicated Retinal Detachments," *American Journal of Ophthalmology*, vol. 102, pp. 20–24 (1986).

Ferrone et al., "The Efficacy of Silicone Oil for Complicated Retinal Detachments in the Pediatric Population," Arch. Ophthalmol., vol. 112, pp. 773–777 (1994).

Hoyle et al., "Photopolymerization of a Semifluorinated Difunctional Liquid Crystalline Monomer in a Smectic Phase," *Macromolecules*, vol. 29, pp. 3182–3187 (1996).

Hoyle et al., "Relating Order and Kinetics in the Photoinitated Polymerization of Liquid Crystalline Monomers," *Proceedings of the American Chemical Society Division of Polymeric Materials: Science and Engineering*, vol. 72, pp. 579–580 (Spring Meeting 1995).

Jariwala et al., "New Hydrophobic and Liquid–Crystalline Fluoroalkyl Ether Derivatives of Ethyl α-(Hydroxymethyl)acrylate: Monomer Synthesis and Polymerization," *Macromolecules*, vol. 24, pp. 6352–6353 (1991).

(List continued on next page.)

*Primary Examiner*—Vivian Chen
*Attorney, Agent, or Firm*—Patrick M. Ryan

[57] ABSTRACT

Coatings for surgical instruments which comprise substituted fluoroalkyl or perfluoroalkyl monomers having anionic, cationic, and/or nonionic surface active functionality in the unsaturated fluorophobic ends.

13 Claims, 1 Drawing Sheet

Jariwala et al., "Syntheses, Polymerization, and Characterization of Novel Semifluorinated Methacrylates, Including Novel Liquid Crystalline Materials," *Macromolecules*, vol. 26, pp. 5129–5136 (1993).

OTHER PUBLICATIONS

Riande et al., "Synthesis and Polarity of Acrylate Polymers with Long Hydrophilic Side Groups," *Macromolecules*, vol. 29, pp. 1728–1733 (1996).

Thomas et al., "Preparation and Surface Properties of Acrylic Polymers Containing Fluorinated Monomers," *Macromolecules*, vol. 30(10), pp. 2883–2890 (1997).

Volkov et al., "Aggregation state and mesophase structure of comb–shaped polymers with fluorocarbon side groups," *Polymer*, vol. 33(6), pp. 1316–1320 (1992).

Volpert et al., "Influence of the Hydrophobe Structure on Composition, Microstructure, and Rheology in Associating Polyacrylamides Prepared by Micellar Copolymerization," *Macromolecules*, vol. 29, pp. 1542–1463 (1996).

Wilson et al., "Measurement of Preretinal Oxygen Tension in the Vitrectomized Human Eye Using Fluorine–19 Magnetic Resonance Spectroscopy," *Arch. Ophthalmol.* vol. 110, pp. 1098–1100 (1992).

Xie et al., Copolymers of N,N–Dimethylacrylamide and 2–(N–ethylperfluorooctanesulfonamido)ethyl Acrylate in Aqueous Media and in Bulk. Synthesis and Properties, *Macromolecules* vol. 29, pp. 1734–1745 (1996).

Yamada et al., "Radical Polymerization and Copolymerization of Methyl$\alpha$–(fluoroalkoxymethyl)acrylates and Characterization of Their Polymers," *J.M.S.–Pure Appl. Chem.*, A29(7), pp. 533–543 (1992).

Jariwala et al., "Photoinitiated Polymerization of Novel Fluoroalkyl Ether Deriviatives of Ethyl $\alpha$–(Hydroxymethyl)acrylate," Polymer Preprints, vol. 34, No. 1(5), pp. 399–400, XP002071758 (1993).

ARTICLES COATED WITH IN VIVO POLYMERIZABLE OPHTHALMIC COMPOSITIONS

This is a continuation-in-part of U.S. Ser. No. 08/833,635 filed Apr. 8, 1997, U.S. Pat. No. 5,858,345, and a continuation-in-part of U.S. Ser. No. 08/825,797 filed Apr. 8, 1997, U.S. Pat. No. 5,905,127, both of which claim the benefit of U.S. Provisional Applications 60/014,925 filed Apr. 8, 1996, and 60/014,926 filed Apr. 8, 1996.

BACKGROUND OF THE INVENTION

1. Field of the Invention

The present invention relates to compositions useful in ophthalmology. In particular, this invention relates to ophthalmic compositions comprising biocompatible, polymerizable, bioadhesive, surface-active, fluorinated monomers. These monomers, spontaneously ordered in vivo to produce liquid-crystalline phases, can be polymerized in situ to repair torn, ruptured or detached retinal tissue.

2. Description of Related Art

Retinal detachments and tears are conventionally repaired using media which exert pressure on the retinal tissues to reposition them such that they are confluent with the underlying tissue, the retinal pigment epithelium (RPE), responsible for nourishing and supporting metabolism of the retinal tissue. Typical repositioning media function as a tamponade, and are ideally neither viscous nor adherent to biological tissue. The density of the repositioning media can be either significantly higher or lower than that of the vitreous body. The principle involves exploiting gravity to maintain approximation of displaced retina at proximal RPE: if the displacement requires upward approximation, then a medium of density less than vitreous is chosen, and if downward, then a medium of density greater than vitreous is chosen. For example, a retinal tear in the macular area may be repositioned using a highly dense media with the patient lying on his back, or with a low density media with the patient lying on his face. If the retinal break is toward the top of the head, repositioning is carried out with gases, and if the break is toward the bottom of the head, repositioning is carried out with media having a high specific gravity.

Examples of repositioning media in use today include silicone oil, fluorocarbon and perfluorocarbon liquids (such as $SF_6$, $C_3F_8$, and $C_2F_6$), nitrogen gas and air. See, for example, Ferrone et al., "The efficacy of silicone oil for complicated retinal detachments in the pediatric population," Arch. Ophthalmol., 112/6, p. 773–777 (1994).

One disadvantage of these conventional techniques is that the resulting reattachment produced by reapproximation using repositioning media often is transient. The desired reattachment often fails upon removal or absorption of the repositioning media. Additionally, the use of dense repositioning media can be awkward, requiring certain positioning of the head to maintain a favorable pressure for attachment. The media may result in complications including scarring, glaucoma, or corneal opacification, or may prove toxic upon extended exposure.

To help prolong the duration of the intended reattachment, once the torn or detached retina is positioned correctly, a procedure called retinopexy can be used to produce adhesion between retina and RPE. Retinopexy can be achieved by using laser, diathermy or cryogenic techniques which induce wounds that stimulate reattachment following the growth of connective tissue. The connective tissue results in rigid attachment of retinal tissue to the RPE. Retinopexy can also be achieved using either biological or nonbiological adhesives such as fibrin or thrombin, or nitrocellulose and cyanoacrylates, respectively. The use of these adhesive materials also results in rigid attachment between retina and RPE. Yet another means of achieving retinopexy involves the use of a "retinal tack." Retinal tacks are typically stainless steel tacks which bind the retina to the RPE. See, for example, De Juan et al., "Mechanical retinal fixation using tacks," Ophthalmology, 94/4, p. 337–340 (1987). Retinopexy, however achieved, can be both painful and temporary. Since the resulting attachments tend to be rigid, possessing considerably larger elastic moduli than the retina itself, normal ocular motions which conventionally are accommodated by the elastic retina can result in new tears and detachments in the vicinity of previous repairs.

What is needed is an alternate means for repairing torn or detached retinal tissue which eliminates inadequacies of the approaches described above.

SUMMARY OF THE INVENTION

The present invention provides a technique for repairing torn or detached retinal tissue. Ophthalmic compositions comprising biocompatible, in vivo polymerizable, bioadhesive monomers are used as a patch for repairing tears in the retina or reattaching detached retinal tissue. The compositions are relatively non-viscous on administration yet sufficiently thixotopic to prevent spontaneous dislocation. Unlike the strong inelastic attachment to underlying tissues provided by retinopexy techniques, the present materials provide distensible reattachment of torn edges of retina. That is, the present material may be stretched without resulting in damage to adjacent or bordering tissue. This in vivo polymerizable composition (or "patch material") of reduced water permeability functions to approximate dislocated tissues. Compared to the retina, the patch material's slightly lower permeability to water assists in anchoring the patch and the retina to which it is attached, reapproximating adjacent retina and the cross-linked polymer to the underlying RPE. The patch material restores retinal continuity and thus restores the normal trans-retinal pressure gradient (approximately 1 mm Hg).

In addition to their application as a material for retinal repair, the novel in vivo polymerizable compositions of the present invention may be useful in a number of other applications, including the correction of hypotony in cases in which vitreous humor is poorly confined by tissue alone, the control of scarring in cases of disruptive surgical intervention, treating retinopathy, and the delivery of pharmaceutically active drugs.

DETAILED DESCRIPTION OF THE INVENTION

Figure 1:
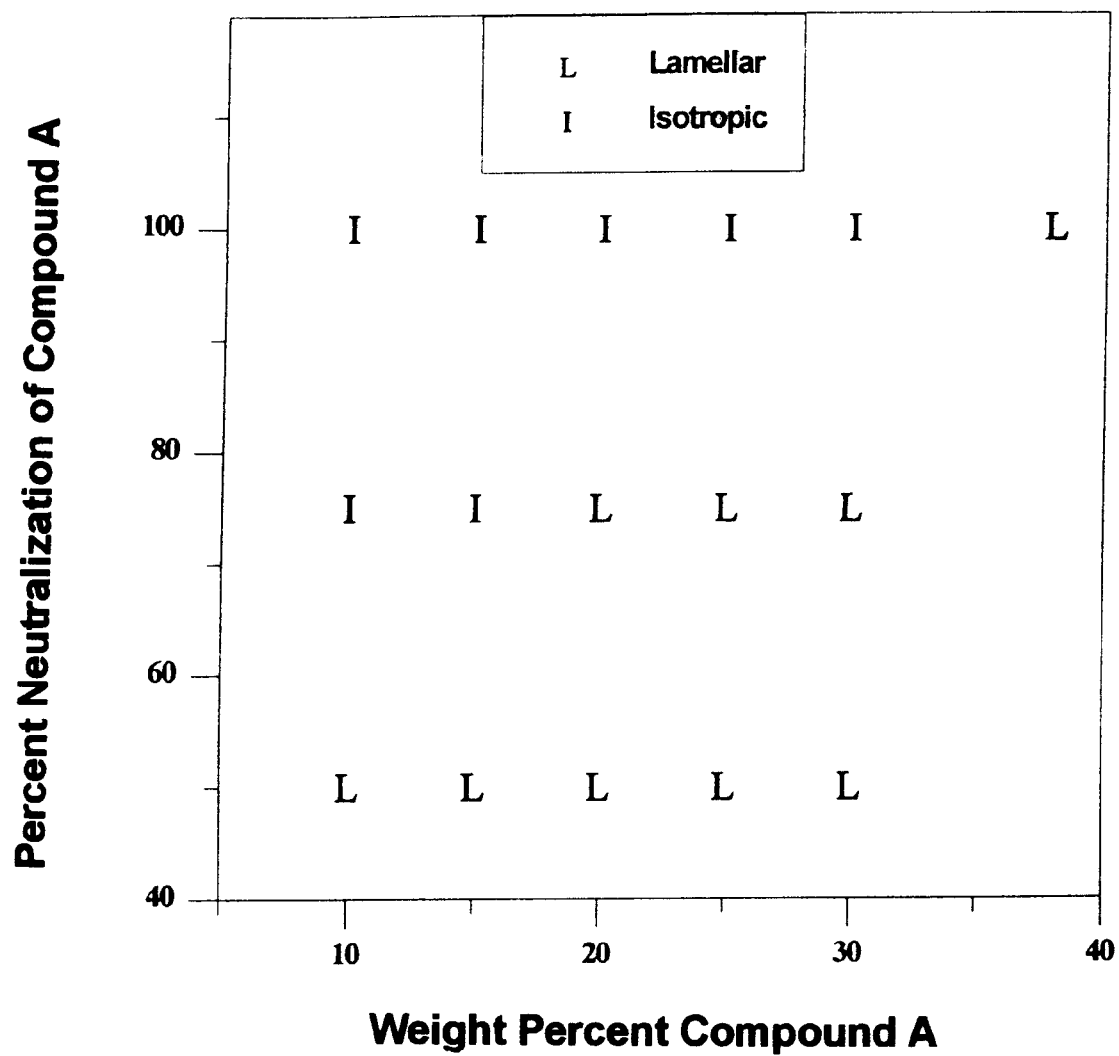
FIG. 1 shows a crude phase diagram for aqueous compositions of Compound A.

In accordance with the present invention, compositions comprising bioadhesive and biocompatible monomers are placed at the site of a retinal tear, remain at that site before polymerizing without contaminating adjacent tissue, and form polymerized strata in vivo. These compositions adhere preferentially to the retina relative to the RPE, and provide a semi-permeable barrier for the transmission of water. The compositions are sufficiently distensible that they neither are dislocated by, nor induce further rupture or tearing of retina as a consequence of, the normal distortions of ocular shape accompanying routine motions and responses to internal or superficial forces.

Before polymerization, the compositions of the present invention comprise substituted fluoroalkyl or perfluoroalkyl monomers, or mixtures of such monomers, and water. The compositions are also preferably neutralized to approximately physiologic pH using ophthalmically acceptable agents, such as NaOH and HCl. The monomers contained in the compositions of the present invention are substituted with different types of "head" groups such that the substituted fluoroalkyl or perfluoroalkyl carbon chains have anionic, cationic, and/or various nonionic hydrophilic functionality at the fluorophobic ends. Additionally, the compositions of the present invention optionally comprise "ABA" block copolymers, where the "A" groups are substituted fluoroalkyl or perfluoroalkyl monomers and the "B" group is a hydrophilic oligomer.

Suitable monomers for use in the compositions of this invention include derivatives of (per)fluoroalkyl ether-substituted hydroxymethacrylic acid and its esters, including those containing alkyl ethoxylated nonionic and anionic substituents, ethoxylated alkyl ammonium substituents, and polyol substituents such as erythritol. In general, these monomers have the general structure shown below. These monomers can be prepared using methods known in the art. See, for example, Jariwala et al., "New Hydrophobic and Liquid-Crystalline Fluoroalkyl Ether Derivatives of Ethyl α-(Hydroxymethyl)acrylate: Monomer Synthesis and Polymerization," *Macromolecules*, Vol. 24, p. 6352–6353 (1991); and Jariwala et al., "Syntheses, Polymerization, and Characterization of Novel Semifluorinated Methacrylates, Including Novel Liquid Crystalline Materials," *Macromolecules*, Vol. 26, p. 5129–5136 (1993).

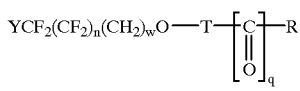

wherein: n is 2–20; w is 1–20; Y is H, F; T is —CH=CH—, —CH$_2$—C(=CH$_2$)—; and q is 0,1

1. R is OH,O$^-$M$^+$
2. R is OCH$_3$

where
R' is H, CH$_3$, CH$_2$CO$_2$H, CH$_2$COO$^-$ M$^+$
m is 1–100;

4. R is NH(CH$_2$)$_n$N(CH$_3$)$_3$$^+$X$^-$
5. R is (OCH$_2$CH$_2$)$_w$N(CH$_3$)$_3$$^+$X$^-$

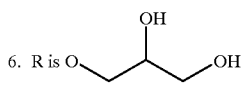

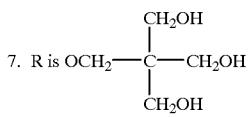

The exact perfluoroalkyl and surface active substituents, and their relative concentrations, are preferably chosen such that the monomers self-assemble into stable thermodynamic liquid-crystalline phases at physiologic temperatures. A favored phase is the lamellar liquid-crystalline phase in which the lamellae consist of alternating hydrophilic and fluorophilic portions, the former associating with aqueous portions and polar portions of membrane lipids, and the latter maintaining segregation from the aqueous environment. A significant increment of stability is imparted by polymerizing the constituent monomer within the mesomorphic phase. This polymerization stabilizes and maintains the anisotropic properties, especially anisotropic viscoelasticity, which are advantageous for retinal repair materials. Such polymerization can be initiated either photochemically, or by oxidation/reduction reactions.

The preferred monomers for use in the materials of the present invention are Compounds 1–7 wherein n is 2–10; w is 1–10; m is 3–50; M$^+$ is Na$^+$; X$^-$ is Cl$^-$; R' is CH$_2$COO$^-$; and q is 1. Preferred compositions of the present invention include mixtures comprising monomers selected from the group consisting of Compounds 1, 3, 4, 6, and 7.

The viscosity of the unpolymerized composition should be characterized by a yield strength and thixotropy such that 1) at rest, the material does not flow under gravity; and 2) under pressure of no more than 80–90 psi, the material will pass through a 20 gage needle.

Alternate liquid-crystalline phases may be utilized for locating the more promising lamellar phase, and may also themselves impart useful rheological characteristics and stability. For example, hexagonal and cubic liquid crystalline phases can be expected at compositions bordering those required to achieve a lamellar phase. The hexagonal and the reversed hexagonal liquid crystalline phases can be expected to occur at lower and higher concentrations, respectively, than the lamellar phase. The hexagonal phase might provide useful ordering and an alternative to that of the lamellar phase. The cubic phase might be achieved on dilution in the eye and could impart desirably high elasticity.

The purpose of the lamellar structure and the perfluorinated alkyl chain is to separate the reaction centers involved in the in situ polymerization reaction from the retinal and underlying tissue, thereby limiting toxicity. Accordingly, one aspect of the present invention is the capacity of the present compositions to be polymerized in situ in a manner that not only maintains spontaneous lamellar liquid-crystalline order but also locks that order into a permanent structure having anisotropic elasticity. Anisotropic elasticity results in a material that is weaker in the axial direction than in the transverse, where the axial direction is presumed to be perpendicular to the tissue surface. This elastic property, together with the lamellar morphology and the bioadhesion imparted by controlling the charge type and fraction of charged monomers, helps produce preferential adherence to the retina over the RPE. The degree of polymerization required will depend in each instance upon the identity and concentrations of the chosen monomers and the nature and extent of the desired patch.

The orientation of these "hemi-fluorinated" polymerizable surfactants to create stable lamellar structures results in alternating oriented sheets of fluorocarbon. These alternating fluorocarbon layers function to limit transport of water through this material because of the insolubility of water in fluorocarbon. While the ionic slip plane, permitting lateral motion of the lamellar sheets, will contain water, the exchange of water between these aqueous lamellae will be restricted. Without being bound to any theory, it is believed that the natural transport of water from vitreous, across retina and out through the RPE results in a natural suction of the retina, and ipso facto the repair material of the present invention, onto the RPE, anchoring the repair material to adjacent retina.

In some instances, it will be advantageous for the polymerized organized structures to be cross-linked. In this regard, the compositions of the present invention optionally comprise block copolymers of the type ABA in which A is predominantly perfluorocarbon (though it may be terminated internally with a nonreactive spacer such as a hydrocarbon) and B is a hydrophilic oligomer, such as polyalkylene glycol. These ABA block copolymers can span hydrophilic layers of the liquid crystalline materials of the present invention with the A termini anchored in the alternating fluorophilic laminae. In this way, the ABA block copolymers can decrease lateral translational motions of the liquid crystalline layers, providing one measure for controlling transverse viscoelasticity and rheology. The partial disordering of the organized structures produced by the ABA block copolymer may improve confluence with adjacent tissue.

Suitable ABA block copolymers useful in the present invention include those of the following structures

I)

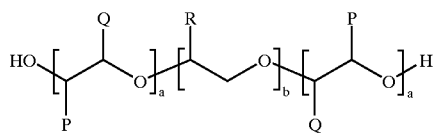

wherein:
P, Q, and R are independently H, $CH_3$;
a and b are independently 1–100;

II) $YCF_2(CF_2)_c(CH_2)_dO(C(T)HCH_2O)_e(CH_2)_d(CF_2)_cCF_2Y$
wherein:
T is H, $CH_3$;
Y is H, F;
c is 1–20;
d is 1–4;
e is 1–100; and

III)

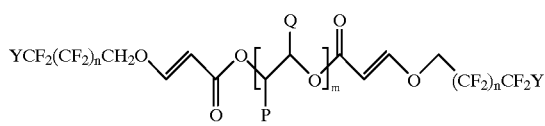

wherein
n is 2–20;
m is 1–100;
Y is H, F; and
P and Q are independently H, $CH_3$.

The compositions of the present invention are expected to possess extended functional lifetimes, both because (i) fluorocarbons resist oxidation and hydrolysis; and (ii) the lamellar structures obtained by the present compositions restrict reactant transport.

The compositions of the present invention are prepared by adding the selected monomer(s) to water and neutralizing the pH to a physiologically acceptable level, generally about 6.8–7.6. It is preferred that the pH be in the range of about 7.3–7.5. In general, the total concentration of monomer(s) in the compositions will range from about 1 to about 60 wt. %. Preferably, the total concentration of monomer(s) will range from about 5 to about 50 wt. %. Most preferably, the total concentration of monomer will range from about 10 to about 35 wt. %. The compositions should be mixed well, and may require moderate heating (to about 50–60° C.), vortexing and/or centrifuging several times. Prior to polymerization, it is preferred to reduce or eliminate as much oxygen as possible by bubbling an inert gas, such as nitrogen gas, through the composition, and then centrifuging the composition.

The unpolymerized compositions of the present invention are delivered to the site in need of repair by intraocular injection. A limited volume of the composition is expressed through a cannula whose tip is positioned at the site of the tear or detachment. The cannula tip may be positioned manually or with the aid of semi-automated surgical instruments, such as microprocessor-controlled apparatus. Only enough material is deposited to substitute for the displaced, dysfunctional or torn retina.

Once positioned at the site to be repaired, the composition of the present invention is polymerized. In vivo polymerization can be accomplished by free radical initiation with either ambient light (e.g., with IR or red end of the visible spectrum) or redox systems (such as those occurring in biological enzymatic catalysis; for example the electron transfer using ferredoxin-NADP reductase). Suitable photoinitiators include biocompatible substituted aromatic photoinitiators. Preferred photoinitiators are those derived from nucleic acids (e.g., cytosine, uracil, and thymidine), porphyrins, steroids, bi-steroids, rhodopsin/retinal, and nitric oxide/nitrones. Suitable redox system initiators include peroxides, such as ammonium-, potassium-, alkyl- or aryl persulfates. As used herein, "in vivo polymerization" encompasses both i) initiating polymerization just prior to administering the polymerizable composition to the site of repair, in which case the polymerization will be completed after administration, and ii) initiating polymerization after the polymerizable composition is delivered to the site of repair. The amount of initiator will be governed by kinetic and toxicity concerns, but in general will be less than about 3 mol %.

Polymerization is desirably confined, or adjacent, to the fluorocarbon lamellae of the phase, and preferably occurs within single layers of the lamellae rather than between them. Covalent linkages between the composition of the present invention and the adjacent tissue should be minimized to reduce the risk that normal eye movement would initiate additional tearing or detachment. The polymerization may be controlled so that only a "light polymerization" is achieved, because the entrapment of non-polymerized neighbors may stabilize the thermodynamic ordering of the phase.

In addition to their applications as retinal repair materials, the compositions of the present invention may also be beneficial in the treatment of hypotony where they may be used to replace dysfunctional retina or other ocular tissue functioning inadequately as a permeability barrier to prevent seepage of water from ocular into adjacent tissue.

Another application for the compositions of the present invention is their use, either alone or in conjunction with therapeutic agents, to suppress exudation and concomitant overgrowth of connective tissue characteristic of proliferative vitreal retinopathy (PVR).

Still another application for the compositions of the present invention is their use as a vehicle in the delivery of therapeutically active drugs. Drugs may be incorporated into the material of the present invention and delivered topically or via injection to targeted sites for prophylactic purposes or in order to control disease in adjacent tissues. For example, such drug delivery may be accomplished utilizing sustained release carriers imbedded in a removable or bioerodible patch comprising the compositions of the present invention.

The compositions of the present invention may also be used to coat surgical instruments, including ophthalmic surgical instruments, and ophthalmic devices, such as drug delivery implants, intraocular lenses, corneal inlays, capsular rings and contact lenses. In some cases, depending on the substrate material of the instrument, it may be necessary or desirable to eliminate or replace the water of the present compositions with another solvent in order to satisfactorily apply the compositions as coatings. As part of the process of applying coatings of the compositions of the present invention, the substituted fluoroalkyl or perfluoroalkyl monomers can be partially or completely polymerized.

Certain embodiments of the present invention are illustrated in the following examples. All percentages are expressed as weight to volume percentages.

EXAMPLE 1

Polymerization of 2-[(2,2,3,3,4,4,5,5,6,6,7,7,8,8,8)-pentadecafluorooctyl-oxy-methyl]-2-propenoic acid. (Also named as [(4,4,5,5,6,6,7,7,8,8,9,9,10,10,10)-pentadecylfluoro-2-oxa-decyl]-2-prop-2-enoic acid; hereinafter "Compound A": Compound 1 where n is 6; w is 1; Y is F; T is —$CH_2$—C(=$CH_2$)—; q is 1; and R is OH).

The polymerization of Compound A was performed in the lyotropic lamellar phase as determined using polarizing microscopy in an aqueous environment. In a typical polymerization, a 28 weight percent (ca. 0.6 M) solution in deionized water was neutralized to approximately 50% through the addition of a calculated amount of sodium hydroxide. After thorough mixing had been achieved, 2 weight percent of potassium persulfate (ca. 0.07 M) as the redox initiator was added to the vial and again the sample was thoroughly mixed. The polymerization process was initiated and conducted by placing the vial containing the sample in an oil bath at 80° C. for 4 hours. The polymerized material was liquid crystalline as determined by polarizing microscopy.

EXAMPLE 2

An ophthalmic composition containing Compound A can be prepared by placing a quantity of the monomer in a suitable reaction container (e.g., plastic round-bottomed centrifuge tubes), adding an appropriate amount of water to obtain a monomer concentration of 30 wt. %, and neutralizing the composition approximately 50% using NaOH and/or HCl so that it will have a pH of approximately 7.3–7.5. The solution is then thoroughly mixed by heating to approximately 50–60° C., vortexing and centrifuging several times.

By utilizing polarizing microscopy, the lyotropic liquid crystalline behavior of concentrated aqueous solutions of Compound A was investigated as a function of the concentration and percent neutralization of Compound A. The results are shown in FIG. 1. At approximately 50% neutralization of the carboxylic acid incorporated in the Compound A monomer, a large lamellar region is found to exist. This is likely a result of an acid-salt bridge between two monomers which effectively increases the size of the hydrophobic tails in relation to the headgroups, thus favoring formation of a lamellar phase. These solutions became increasingly hazy as the concentration of Compound A was increased. At 75% neutralization, a lamellar phase was again found but at higher concentrations of Compound A. As more of the acid groups are neutralized, there will be fewer acid-salt interactions which in turn lowers the stability of the lamellar phase at low surfactant Compound A concentrations. Finally, at 100% neutralization, much higher concentrations of Compound A are required to achieve a lamellar mesophase. These studies were conducted in deionized water at room temperature and differences in phase boundaries are expected to occur: 1) at higher temperatures and 2) in aqueous solutions containing additives (i.e., electrolytes).

Only those compositions with appropriate degrees of neutralization to provide physiologically acceptable pH will be adequate for intraocular administration of the sterile compositions.

EXAMPLE 3

An ophthalmic composition according to the present invention will contain 40% water, 50% of Compound 1 (n is 6; $M^+$ is $Na^+$; w is 1; Y is F; T is —CH=CH—; and q is 1: the sodium salt of the acid, 4-oxa-6,6,7,7,8,8,9,9,10,10,10-undecafluoro decanoic acid) and 10% of Compound 3 (n is 6; m is 15; w is 1; Y is F; R' is $CH_2COO^-$; $M^+$ is $Na^+$; T is —CH=CH—; and q is 1). The solution will exhibit birefringence when studied with polarizing microscopy; analysis of the optical texture by conoscopy will indicate the phase is lamellar and this will be confirmed by its powder pattern (observed using x-ray crystallography).

EXAMPLE 4

An ophthalmic composition according to the present invention will contain 40% water, 50% of Compound 1 (n is 6; $M^+$ is $Na^+$; w is 1; Y is F; T is —CH=CH—; and q is 1) and 10% of Compound 3 (n is 6; m is 15; w is 1; Y is F; R' is $CH_2COO^-$; $M^+$ is $Na^+$; T is —CH=CH—; and q is 1). The solution will exhibit birefringence when studied with polarizing microscopy; analysis of the optical texture by conoscopy will indicate the phase is lamellar and this will be confirmed by its powder pattern (observed using x-ray crystallography). To this mixture will be added a mixture of equal amounts of Compounds 6 and 7 (n is 6; w is 1; Y is F; T is —CH=CH—; and q is 1, for both) used to tune the elasticity of the subsequently polymerized material to a G' of approximately 2 kPa.

EXAMPLE 5

An ophthalmic composition according to the present invention will contain 40% water, 53% of Compound 1 (n is 6; $M^+$ is $Na^+$; w is 1; Y is F; T is —CH=CH—; and q is 1), and 7% of Compound 3 (n is 8; m is 20; w is 1; Y is F; R' is $CH_2COO^-$; $M^+$ is $Na^+$; T is —CH=CH—; and q is 1). The solution will exhibit birefringence when studied with polarizing microscopy; analysis of the optical texture by conoscopy will indicate the phase is lamellar and this will be confirmed by its powder pattern (observed using x-ray crystallography).

EXAMPLE 6

An ophthalmic composition according to the present invention will contain 40% water, 53% of Compound 4 (n is 8; w is 1; Y is F; X⁻ is Cl⁻; T is —CH=CH—; and q is 1), and 7% of Compound 3 (n is 8; m is 15; w is 1; Y is F; R' is CH₂COO⁻; M⁺ is Na⁺; T is —CH=CH—; and q is 1). The solution will exhibit birefringence when studied with polarizing microscopy; analysis of the optical texture by conoscopy will indicate the phase is lamellar and this will be confirmed by its powder pattern (observed using x-ray crystallography).

EXAMPLE 7

An ophthalmic composition according to the present invention will contain 40% water, 28% Compound 1 (n is 6; M⁺ is Na⁺; w is 1; Y is F; T is —CH=CH—; and q is 1), 25% of Compound 4 (n is 8; w is 1; Y is F; X⁻ is Cl⁻; T is —CH=CH—; and q is 1), and 7% Compound 3 (n is 8; m is 15; w is 1; Y is F; R' is CH₂COO⁻; M⁺ is Na⁺; T is —CH=CH—; and q is 1). The solution will exhibit birefringence when studied with polarizing microscopy; analysis of the optical texture by conoscopy will indicate the phase is lamellar and this will be confirmed by its powder pattern (observed using x-ray crystallography).

EXAMPLE 8

An ophthalmic composition according to the present invention will contain 40% water, 27% Compound 1 (n is 6; M⁺ is Na⁺; w is 1; Y is F; T is —CH=CH—; and q is 1), 24% of Compound 4 (n is 8; w is 1; Y is F; X⁻ is Cl⁻; T is —CH=CH—; and q is 1); 7% Compound 3 (n is 8; m is 15; w is 1; Y is F; R' is CH₂COO⁻; M⁺ is Na⁺; T is —CH=CH—; and q is 1); and 2% of the ABA block copolymer $C_8F_{15}(OCH_2CH_2)C_8F_{15}$. The solution will exhibit birefringence when studied with polarizing microscopy; analysis of the optical texture by conoscopy will indicate the phase is lamellar and this will be confirmed by its powder pattern (observed using x-ray crystallography).

EXAMPLE 9

The polymerization of the ophthalmic composition of Example 2 above was performed in the lyotropic lamellar phase as determined from polarizing microscopy in an aqueous environment. Polymerization was initiated using 0.5 mol % of ammonium persulfate. The ammonium persulfate was added as a solid, then the composition was mixed again without heating. Finally, 0.5 mol % TEMED (tetramethylethylethylenediamine) was mixed into the composition as an accelerator and the reaction vessel was placed in a water bath at approximately 37° C.

EXAMPLES 10–14

Five additional 2-ml-sized compositions according to Example 2 above were prepared and polymerized as shown in Table 1 below. Prior to polymerization, nitrogen was bubbled through all five compositions in order to remove oxygen, after which the compositions were briefly mixed without heating. As expected, the polymerization rate was dependent upon the existence and concentration of polymerization initiators and acceleration agents. Whereas prior to polymerization, the compositions appeared homogeneous and clear, after the indicated time periods, the polymerized compositions in some instances separated into a less dense, non-viscous, aqueous top phase and a solid-like, firm, clear or opaque, gelled bottom phase. In other instances, the entire sample gelled. In both instances, the gels were observed to fracture along parallel cleavage planes. These results are displayed in Table 2 below.

TABLE 1

| Example No. | Conc. (%) | % Neutrality | pH (measured) | Polymerization Time | Excess Initiator Used | Excess Accelerator Used |
| --- | --- | --- | --- | --- | --- | --- |
| 10 | 10 | 50.4 | 7.27 | >2 hrs. | 5 x | 13 x |
| 11 | 15 | 49.8 | 7.12 | 45 min. | 1.7 x | 12.5 x |
| 12 | 20 | 50.0 | 7.34 | Overnight | — | 8 x |
| 13 | 25 | 50.0 | 6.82 | 15 min. | 3 x | 7.5 x |
| 14 | 30 | 50.0 | 7.36 | 10 min. | 2.5 x | 6.25 x |

TABLE 2

| | Appearance Post-Polymerization | |
| --- | --- | --- |
| Example No. | # of Phases | Color |
| 10 | 2 | clear |
| 11 | 1 | clear |
| 12 | 1 | yellowish |
| 13 | 2 | polymerized phase slightly yellow |
| 14 | 1 | slightly yellow |

EXAMPLE 15

The compositions of Examples 3–8 can be polymerized utilizing complexed iron at a concentration of 45 mg/dL of iron. (Iron in the +2 oxidation state can be used to generate oxygen radicals which in turn are used to produce acrylate free radicals and initiate polymerization.) After polymerization, the liquid-crystalline morphology of the materials should be preserved. Approximate values for G' (axial) and G' (transverse) will be greater that 0.1 kPa and 0.3 kPa, respectively.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A coated surgical instrument wherein the coating comprises a polymerizable monomer of the structure

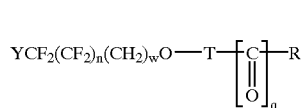

(I)

wherein n is 2–20;
w is 1–20;
q is 0, 1;
Y is H, F;
T is —CH=CH—, —CH$_2$—C(=CH$_2$)—;
R is OH, O$^-$M$^+$, OCH$_3$, NH(CH$_2$)$_n$N(CH$_3$)$_3$$^+$X$^-$, (OCH$_2$CH$_2$)$_w$N(CH$_3$)$_3$$^+$X$^-$, OCH$_2$C(CH$_2$OH)$_3$,

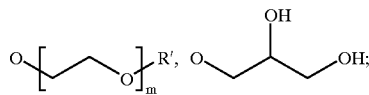

R' is H, CH$_3$CH$_2$CO$_2$H, CH$_2$COO$^-$M$^+$;
m is 1–100;
M$^+$ is a pharmaceutically acceptable cation; and
X$^-$ is a pharmaceutically acceptable anion, and the coating further comprises a compound selected from the group consisting of

I)

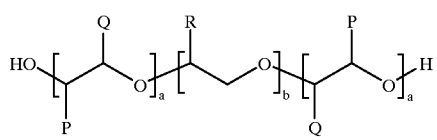

wherein:
P, Q, and R are independently H, CH$_3$;
a and b are independently 1–100;

II) YCF$_2$(CF$_2$)$_c$(CH$_2$)$_d$O(C(T)HCH$_2$O)$_e$(CH$_2$)$_d$(CF$_2$)$_c$CF$_2$Y wherein:
T is H, CH$_3$;
Y is H, F;
c is 1–20;
d is 1–4;
e is 1–100; and

III)

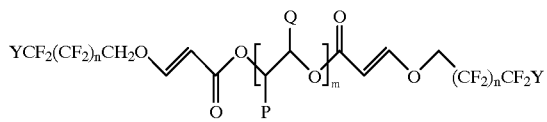

wherein
n is 2–20;
m is 1–100;
Y is H, F; and
P and Q are independently H, CH$_3$.

2. The coated surgical instrument of claim 1 wherein the coating comprises the compound of the structure

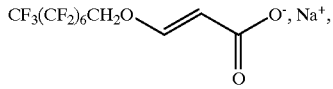

and the compound of the structure

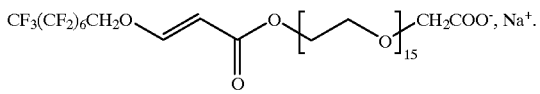

3. The coated surgical instrument of claim 2 wherein the coating further comprises the compound of the structure

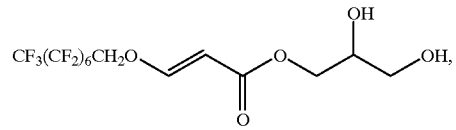

and the compound of the structure

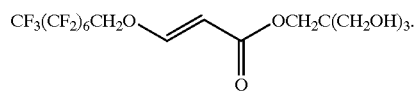

4. The coated surgical instrument of claim 1 wherein the coating comprises the compound of the structure

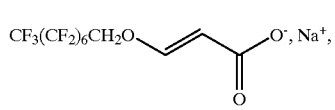

and the compound of the structure

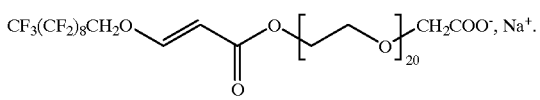

5. The coated surgical instrument of claim 1 wherein the coating comprises the compound of the structure

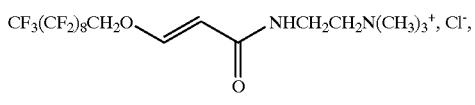

and the compound of the structure

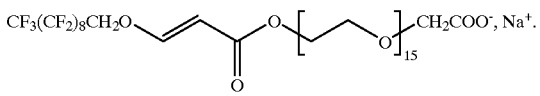

6. The coated surgical instrument of claim 1 wherein the coating comprises the compound of the structure

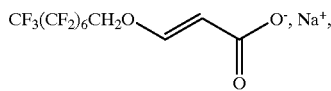

and the compound of the structure

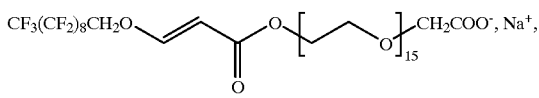

and the compound of the structure

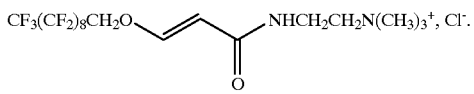

7. The coated surgical instrument of claim 1 wherein the coating comprises the compound of the structure

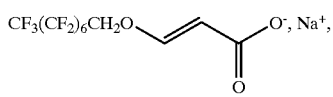

the compound of the structure

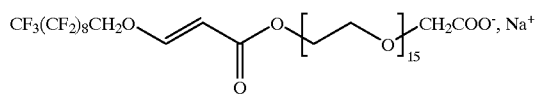

the compound of the structure

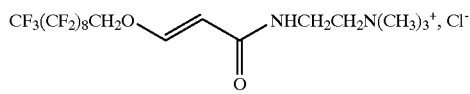

and the ABA block copolymer $C_8F_{15}(OCH_2CH_2)C_8F_{15}$.

8. A coated ophthalmic device wherein the coating comprises a polymerizable monomer of the structure

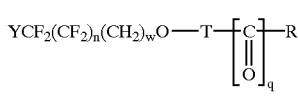
(I)

wherein
  n is 2–20;
  w is 1–20;
  q is 0, 1;
  Y is H, F;
  T is —CH=CH—, —CH$_2$—C(=CH$_2$)—;
  R is OH, O$^-$M$^+$, OCH$_3$, NH(CH$_2$)$_n$N(CH$_3$)$_3^+$X$^-$, (OCH$_2$CH$_2$)$_w$N(CH$_3$)$_3^+$X$^-$, OCH$_2$C(CH$_2$OH)$_3$,

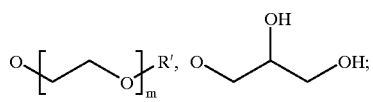

R' is H, CH$_3$CH$_2$CO$_2$H, CH$_2$COO$^-$M$^+$;
  m is 1–100;
  M$^+$ is a pharmaceutically acceptable cation; and
  X$^-$ is a pharmaceutically acceptable anion, and the coating further comprises a compound selected from the group consisting of

I)

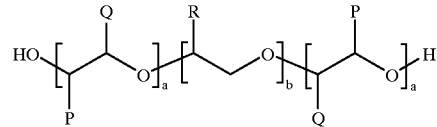

wherein:
  P, Q, and R are independently H, CH$_3$;
  a and b are independently 1–100;

II) YCF$_2$(CF$_2$)$_c$(CH$_2$)$_d$O(C(T)HCH$_2$O)$_e$(CH$_2$)$_d$(CF$_2$)$_c$CF$_2$Y wherein:
  T is H, CH$_3$;
  Y is H, F;
  c is 1–20;
  d is 1–4;
  e is 1–100; and

III)

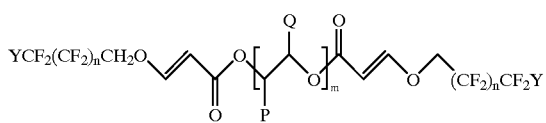

wherein
  n is 2–20;
  m is 1–100;
  Y is H, F; and
  P and Q are independently H, CH$_3$.

9. The coated ophthalmic device of claim 8 wherein the coating comprises the compound of the structure

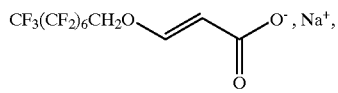

and the compound of the structure

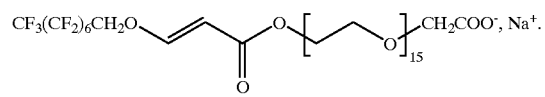

10. The coated ophthalmic device of claim 9 wherein the coating further comprises the compound of the structure

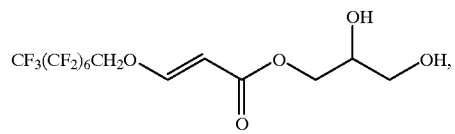

and the compound of the structure

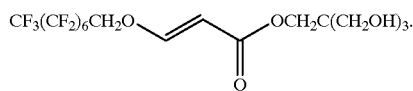

11. The coated ophthalmic device of claim 8 wherein the coating comprises the compound of the structure

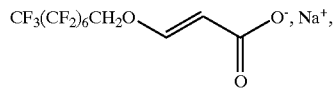

and the compound of the structure

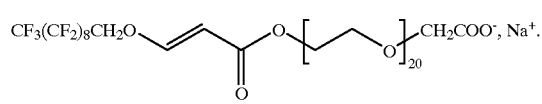

12. The coated ophthalmic device of claim 8 wherein the coating comprises the compound of the structure

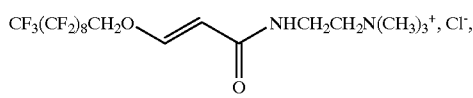

and the compound of the structure

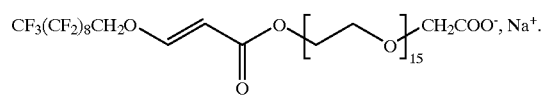

13. The coated ophthalmic device of claim 8 wherein the coating comprises the compound of the structure

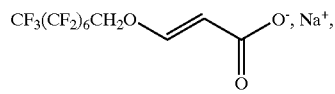

and the compound of the structure

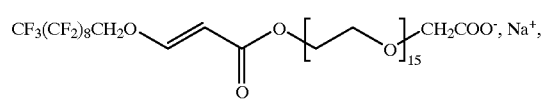

and the compound of the structure

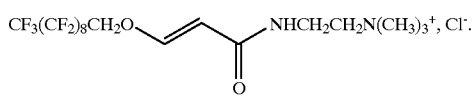

* * * * *